(12) United States Patent
Tam (10) Patent No.: US 6,574,297 B2
(45) Date of Patent: Jun. 3, 2003

(54) SYSTEM AND METHOD FOR IMAGE RECONSTRUCTION IN A CONE BEAM IMAGING SYSTEM

(75) Inventor: Kwok Tam, Edison, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 20 days.

(21) Appl. No.: 10/015,716

(22) Filed: Oct. 30, 2001

(65) Prior Publication Data

US 2003/0081715 A1 May 1, 2003

(51) Int. Cl.[7] ................................................. A61B 6/03
(52) U.S. Cl. .............................. 378/15; 378/8; 378/901
(58) Field of Search .......................... 378/4, 8, 15, 901

(56) References Cited

U.S. PATENT DOCUMENTS

| | | | |
|---|---|---|---|
| 5,257,183 A | 10/1993 | Tam | 364/413.19 |
| 5,463,666 A | 10/1995 | Eberhard et al. | 378/4 |
| 5,504,792 A | 4/1996 | Tam | 378/15 |
| 5,748,697 A | 5/1998 | Tam | 378/19 |
| 5,881,123 A | 3/1999 | Tam | 378/4 |
| 5,926,521 A | 7/1999 | Tam | 378/4 |
| 6,009,142 A * | 12/1999 | Sauer et al. | 378/15 |
| 6,018,561 A | 1/2000 | Tam | 378/4 |
| 6,084,937 A * | 7/2000 | Tam et al. | 378/4 |
| 6,130,930 A | 10/2000 | Tam | 378/4 |
| 6,324,245 B1 * | 11/2001 | Tam | 378/4 |
| 6,333,960 B1 * | 12/2001 | Tam | 378/15 |

\* cited by examiner

Primary Examiner—David V. Bruce
(74) Attorney, Agent, or Firm—Donald B. Paschburg; F. Chau & Associates, LLP (57) ABSTRACT

A system and method for accurately reconstructing an image of a ROI (region of interest) within a long object by removing components associated with data contamination. In one aspect, an image reconstruction method comprises collecting a set of image data along a spiral scan path of a ROI (region of interest) portion of an object, identifying contaminated data within the collected set of image data, the contaminated data corresponding to image data associated with an object outside the ROI, and reconstructing an image of the ROI using the set of image data less the contaminated data.

18 Claims, 9 Drawing Sheets

SYSTEM AND METHOD FOR IMAGE RECONSTRUCTION IN A CONE BEAM IMAGING SYSTEM

BACKGROUND

1. Technical Field

The present invention relates generally to a system and method for 3-dimensional (3D) image reconstruction in a spiral scan cone beam computed tomography (CT) imaging system and, more specifically, to a spiral scan cone beam CT system and method that accurately reconstructs an image of a ROI (region of interest) within a long object by removing components associated with data contamination.

2. Description of Related Art

A system employing cone beam geometry has been developed for three-dimensional (3D) computed tomography (CT) imaging that comprises a cone beam x-ray source and a 2D area detector. An object to be imaged is scanned, preferably over a 360 degree angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

Various methods have been developed for 3D image reconstruction for cone beam x-ray imaging systems. For example, a filtered backprojection (FBP) cone beam image reconstruction technique is described by Kudo, H. and Saito, T., in their article entitled "Derivation and Implementation of a Cone-Beam Reconstruction Algorithm for Nonplanar Orbits", IEEE Trans.Med, Imag., MI-13 (1994) 196–211.

Figure 1A:
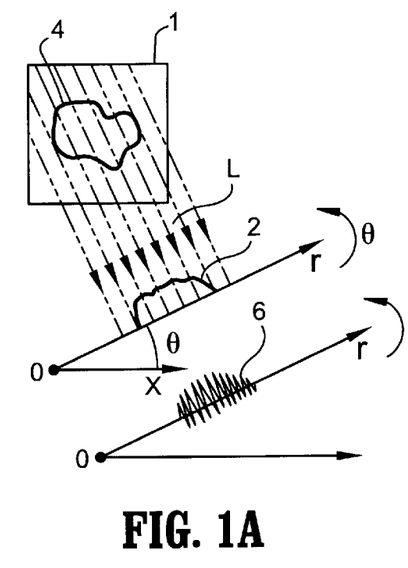
FIGS. 1A and 1B illustrate a conventional 3D backprojection method for cone beam image reconstruction.
Figure 1B:
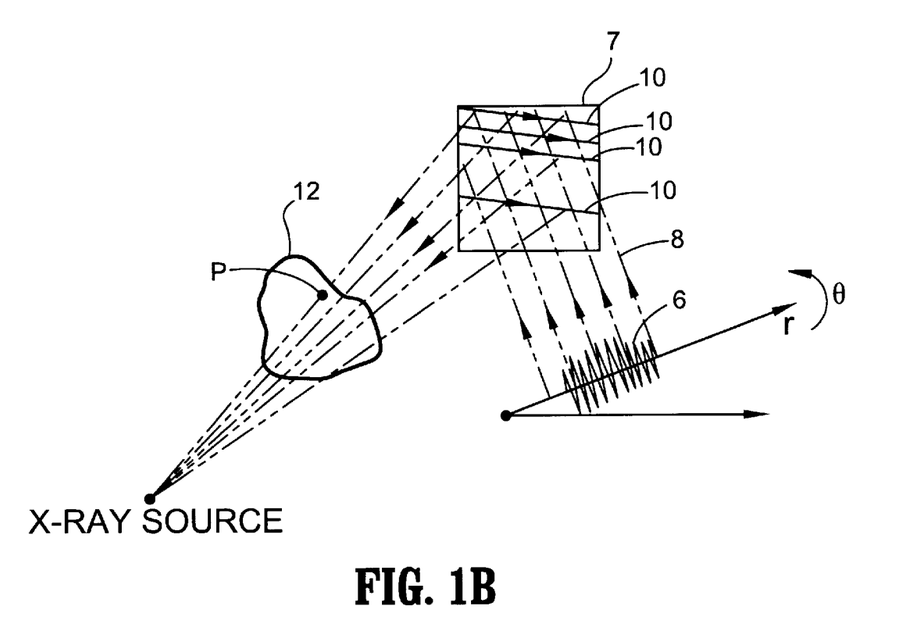

Briefly, the FBP technique comprises the following steps at each cone beam view (i.e., at each position of the radiation source as it scans about the object, and at which an imaging detector acquires a corresponding set of projection data):

1. Compute a 1-dimensional projection (i.e., line integral) of the measured cone beam image acquired on a detector plane 1 at each of a plurality of angles 2. This step is illustrated by FIG. 1A for a given angle $2_1$ of a plurality of angles 2, where the projection 2 at coordinates (r, 2) comprises the integrated values of the cone beam image 4 on detector plane 1 along a plurality of parallel lines L(r, 2) that are normal to angle 2, each line L being at an incremental distance r from an origin O. Generally, if the detector plane 1 comprises an N by N array of pixels, then the number of angles 2 is typically given by BN/2.
2. Filter each 1D projection in accordance with a d/dr filter, resulting in a new set of values at each of the r, 2 coordinates, such as shown by filtered projection 6 for the angle $2_1$ in FIG. 1A.
3. Normalize the filtered projections with a normalization function M(r, 2). Normalization is needed to take into account the number of times the plane of integration Q(r, 2) which intersects the source position and the line L(r, 2), intersects the scan path, since the data developed at each scan path intersection creates a contribution to the image reconstruction on the plane Q(r, 2).
4. Backproject the filtered projection 6 from each angle 2 into a 2D object space 7 that coincides with the detector plane 1. This step is illustrated by FIG. 1B, wherein lines 8 spread the value from each r, 2 coordinate into 2D space 7 in a direction normal to each 2.
5. Perform a 1D d/dt filtering of the backprojection image formed in 2D space 7 by step 4. The 1D filtering is performed in the direction of the scan path, i.e., along lines 10, where the arrowhead points in the direction of the scan path.
6. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the spatial coordinates of the x-ray source (see Equation (59) of the forenoted Kudo et al article).

The above procedure will be referred to hereinafter as the 6-step process. It is assumed in this process that the entire cone beam image of the object is captured on the detector of the imaging system. Consider a plane Q(r, 2), which intersects the object, formed by the source and the line L(r, 2) on the detector at angle 2 and at a distance r from the origin. Ignoring the function M(r, 2), the operations 1 through 6 compute the contribution to the reconstructed object density on the plane Q(r, 2) from the x-ray data illuminating the plane and its immediate vicinity. Since the 6-step process is detector driven, a contribution from the data illuminating the plane is computed every time the plane intersects the scan path and thus is illuminated by the x-ray beam. Consequently, the function M(r, 2) is used after the filter function in step 2 to normalize the results. Normalization is particularly undesirable since it requires pre-computing and storing a 2D array M(r, 2) for each source position along an imaging scan path. Since there are usually hundreds, if not thousands of source positions, this type of normalization is both computationally intensive and resource (computer memory) expensive.

As well known, and fully described for example in U.S. Pat. No. 5,257,183 entitled: METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT, issued Oct. 26, 1993, incorporated herein by reference, one known method of image reconstruction processing generally begins by calculating Radon derivative data from the acquired cone beam data. The Radon derivative data is typically determined by calculating line integrals for a plurality of line segments L drawn in the acquired cone beam data. In the embodiment described in detail in the U.S. Pat. No. 5,257,183 patent, Radon space driven conversion of the derivative data is used to develop an exact image reconstruction of a region-of-interest (ROI) in the object.

A cone beam data masking technique which improves the efficiency of the calculation of the Radon derivative data in such a Radon space driven technique is described in U.S. Pat. No. 5,504,792 entitled METHOD AND SYSTEM FOR MASKING CONE BEAM PROJECTION DATA GENER- ATED FROM EITHER A REGION OF INTEREST HELICAL SCAN OR A HELICAL SCAN, issued Apr. 2, 1996, also incorporated herein by reference. The masking technique facilitates efficient 3D CT imaging when only the ROI in the object is to be imaged, as is normally the case. In the preferred embodiment described therein, a scanning trajectory is provided about the object, the trajectory including first and second scanning circles positioned proximate the top and bottom edges, respectively, of the ROI, and a spiral scanning path is connected therebetween. The scanning trajectory is then sampled at a plurality of source positions where cone beam energy is emitted toward the ROI. After passing through the ROI the residual energy at each of the source positions is acquired on an area detector as a given one of a plurality of sets of cone beam data. Each set of the cone beam data is then masked so as to remove a portion of the cone beam data that is outside a given sub-section of a projection of the ROI in the object and to retain cone beam projection data that is within the given sub-section. The shape of each mask for a given set of cone beam data is determined by a projection onto the detector of the scan path which is above and below the source position which acquired the given set of cone beam data. The masked (i.e., retained) cone beam data is then processed so as to develop reconstruction data. An exact image of the ROI is developed by combining the reconstruction data from the various source positions which intersect a common integration plane. Hence, the masks are commonly referred to as "data-combination" masks.

Data-combination masks can also be used to improve the efficiency of the calculation of the derivative data in a detector data driven technique, such as the simplified ramp filter technique described in U.S. Pat. No. 5,881,123 entitled SIMPLIFIED CONE BEAM IMAGE RECONSTRUCTION USING 3D BACKPROJECTION, issued Mar. 9, 1999, also incorporated herein by reference. This technique reconstructs the image using 2D approximation data sets formed by ramp filtering the masked cone beam data in the direction of the projection of a line drawn tangent to the scan path at the source position that acquired that set of cone beam data. Although this technique is less complex than the prior techniques, the reconstructed image is not exact.

In U.S. Pat. No. 5,926,521, entitled EXACT REGION OF INTEREST CONE BEAM IMAGING USING 3D BACKPROJECTION, issued on Jul. 20, 1999, which is commonly assigned and incorporated herein by reference, a technique is introduced which departs from the conventional Radon space driven conversion processing techniques for image reconstruction (such as known by U.S. Pat. Nos. 5,257,183 and 5,463,666), and provides a mechanism to incorporate the technique of data combination for region-of-interest (ROI) reconstruction, with the Kudo et al. image reconstruction processing, thereby providing an image reconstruction technique for a cone beam imaging system that can not only have a spiral scan path, but can also use a short detector, With this technique, instead of division by the function M(r, 2) as done by Kudo et al., the effect of the normalization of the reconstructed object densities is achieved by dividing the x-ray beam coverage of integration plane Q(r, 2) between the various source positions that illuminate the plane without any overlap.

More specifically, this technique comprises a 4 step process:

1. Apply a mask to the set of cone beam projection data acquired by the detector at each of the source positions, so that only specific non-overlapping contributions to the Radon data can be developed from the projection data.

2. Calculate line integral derivatives in the masked data.
3. Perform a 2D backprojection of the derivative data onto an extended height virtual detector.
4. Perform a 3D backprojection of the 2D data from the virtual detector into a 3D object space.

The presence of a detector mask ensures that the contributions developed by processing projection data of the different detectors are unique and non-redundant (FIG. 1 of this disclosure). Accordingly, division by the function M(r, 2), or its equivalent, is no longer needed, which is a significant simplification in the image reconstruction signal processing. However, although step 2, is not complex, it is computationally expensive. More specifically, it comprises calculating a plurality of line integrals L(r, 2) on each set of the masked detector data, to generate sampled 1D projections of the detector data. Line integral derivatives are then computed from the 1D projections by taking the difference between parallel line segments L1 and L2, as shown in mask 20 of FIG. 2 herein. Note that the L1 and L2 line segments are not limited by the boundaries of the mask 20, and therefore their use results in an exact calculation for the derivatives of line integrals L(r, 2). This type of masking is referred to herein as "soft masking". Additional details of such soft masking can be found in U.S. Pat. No. 5,748,697, incorporated herein by reference. Step 3 backprojects the line integral derivatives onto the extended "virtual" detector. Before the 3D backprojection in step 4, the gradient of the backprojected virtual detector data in the direction of the scan path is calculated, and the result is then backprojected into the 3D object space for reconstruction the ROI of the object. For good image quality, the sampling of the projections and the number of source positions needs to be very fine. Thus, the filter process described in U.S. Pat. No. 5,926,521 is computationally costly.

Figure 3:
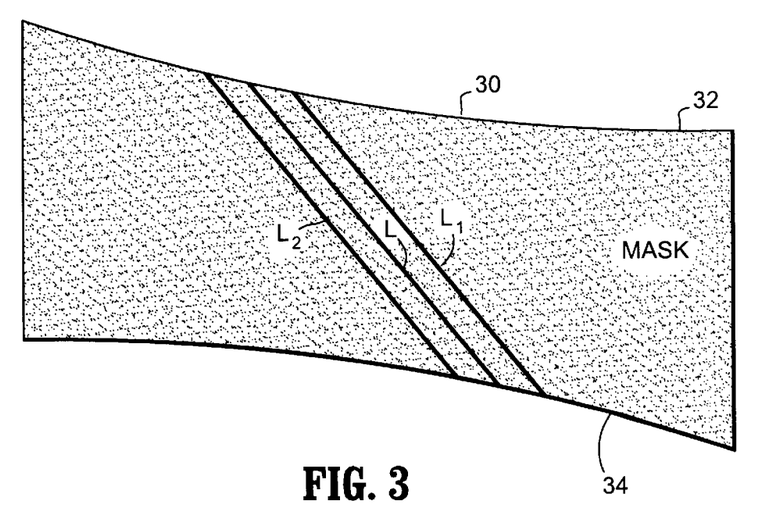

In the above incorporated U.S. Pat. No. 5,881,123 entitled SIMPLIFIED CONE BEAM IMAGE RECONSTRUCTION USING 3D BACKPROJECTION, a Feldkamp convolution processing simplification (also referred to as ramp filtering) is implemented with the above-described image reconstruction processing, wherein the entire filter process described in U.S. Pat. No. 5,926,521 is replaced with a single step of ramp filtering of the detector data in the direction of the scan path. This simplification is illustrated in FIG. 3, where L, L1' and L2' are three closely spaced parallel line segments that are bound by a mask 30, and L is midway between L1' and L2'. Line segment L is representative of many such line segments formed at various angles in mask 30, and corresponds to the previously described lines L (r, 2) of FIG. 1, which as well known to those skilled in this technology are used for computing Radon derivative data from the cone beam projection data. In the technique described in U.S. Pat. No. 5,881,123, due to the bounding of the line segments L1' and L2' by mask 30, the Feldkamp convolution processing simplification (referred to as ramp filtering) is performed as a substitute for the line integral derivative calculations, which filter A processing corresponds to calculation of the Radon derivative of the partial plane defined by the line segment L and the current source position, up to a multiplicative constant.

Figure 2:
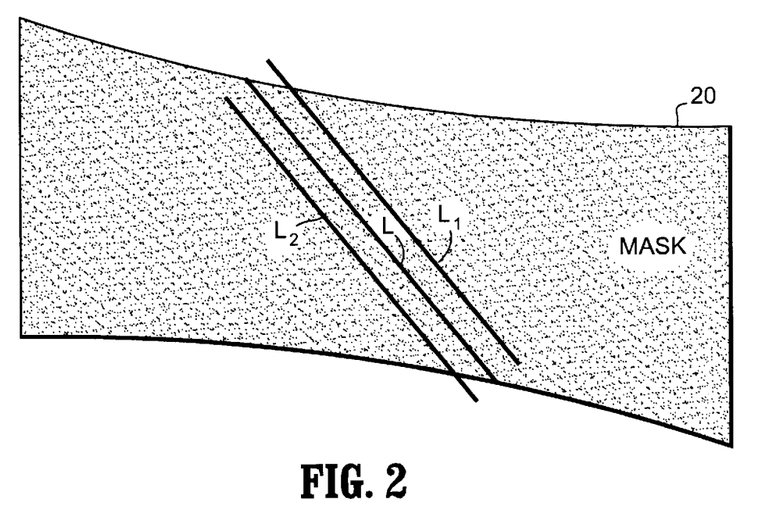
FIGS. 2 and 3 illustrate soft and hard masking, respectively, each technique useful for developing Radon derivative data from the acquired cone beam projection.

Although this operation is computationally very fast, it yields only an approximation of the Radon derivative of the partial plane, due to errors that come about due to the "hard masking" of the endpoints of line segments L1' and L2' by mask 30, as compared to the "soft" masking shown in FIG. 2. That is, it incorrectly limits the detector pixel values to those pixels that are in the mask area, and zeros out the detector pixel values that are outside of the mask boundaries, instead of correctly limiting only the line segments L to the mask area (and calculating the line integral derivatives using the unmasked original detector data when appropriate, i.e., near the mask boundaries).

Accordingly, in U.S. Pat. No. 6,018,561, entitled: MASK BOUNDARY CORRECTRION IN A CONE BEAM IMAGING SYSTEM USING SIMPLIFIED FILTERD BACKPROJECTION IMAGE RECONSTRUCTION, which is incorporated herein by reference, the present inventor describes a technique for computing 2D correction data which, when combined with the ramp filtered 2D approximation data sets, yields an exact image reconstruction. As described in greater detail in U.S. Pat. No. 6,018,561, the mathematical difference between hard and soft masking, which involves only detector data around the mask boundaries, is calculated to arrive at an additive correction term.

Figure 5:
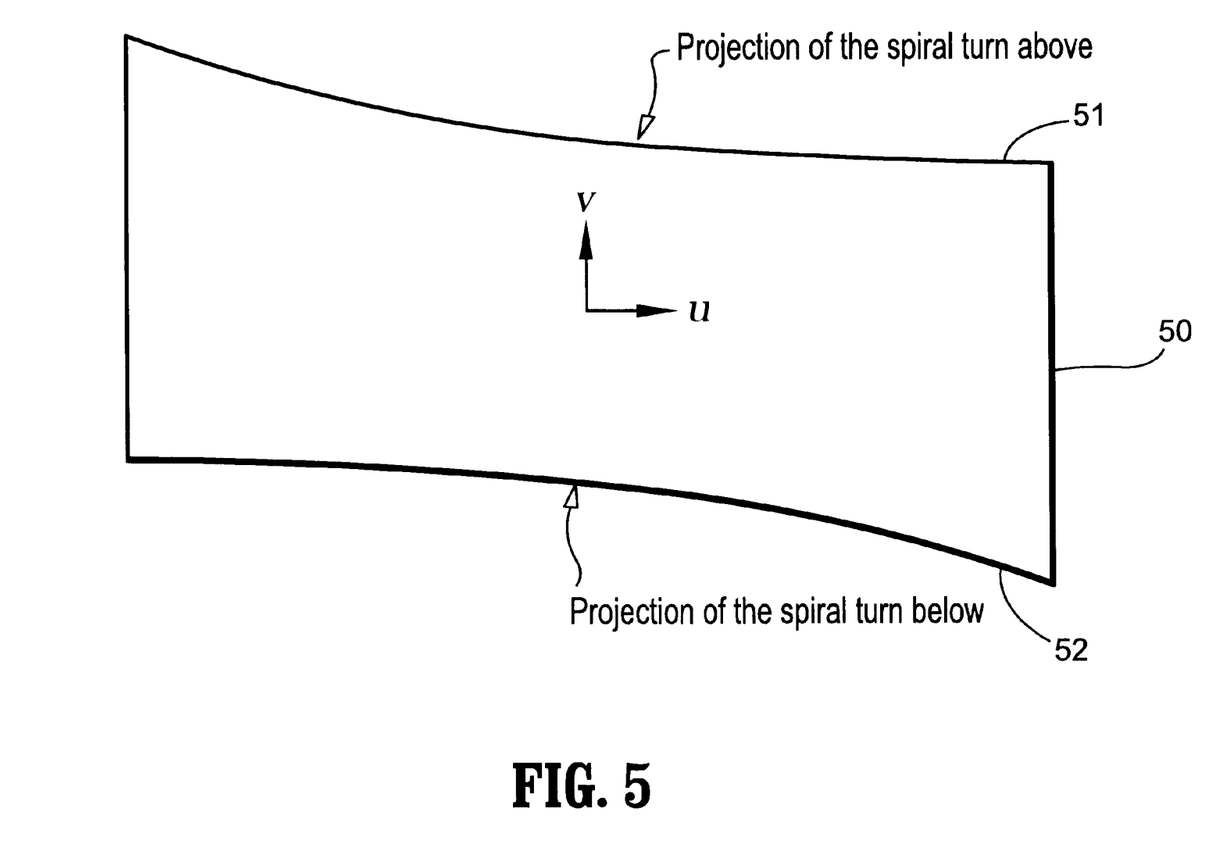
FIG. 5 illustrates an exemplary spiral mask on a flat detector for data combination.

More specifically, in U.S. Pat. No. 6,018,561, it was determined in that when the spiral scan path extends beyond both ends of the object, exact image reconstruction can be achieved with the following operations:

Step 1: Mask the cone beam data. This step comprises applying a spiral mask (such as shown in FIG. 5) to each set of the projection data so that data inside the boundaries of each mask form a corresponding plurality of masked 2D data sets.

Step 2: 1D Ramp filter cone beam data in interior of mask in the direction of scan path. This step comprises ramp filtering each masked 2D set along a plurality of parallel lines formed therein, to generate a corresponding plurality of filtered 2D data, each filtered 2D data set corresponding to a calculation of a first estimate of Radon derivative data determined from a given set of the 2D cone beam projection data.

Step 3: 2D filter cone beam data on mask boundary. This step comprises generating 2D correction data for each of the first estimates of Radon derivative data by processing portions of the given set of cone beam projection data that are adjacent boundaries of the mask. The result is referred to as the boundary/correction term.

Step 4: Image reconstruction. This step comprises performing a weighted 3D backprojection of the filtered cone beam data from each pixel on the detector onto the 3D object volume. In particular, this step comprises combining each filtered 2D data set and the 2D correction data calculated therefore, via a weighted 3D backprojection protocol into a 3D space, thereby reconstructing a 3D image of the ROI in the object. Each of these steps is described in further detail below and in the above-incorporated U.S. Pat. No. 6,018,561.

The above 4-step algorithm (referred to herein as the "short object algorithm") provides accurate image reconstruction when the entire object is the ROI (i.e., the spiral scan extends past the ends of the object). There are various objects of interest in medical as well as industrial inspections, however, that are very long, relatively speaking. For example, a patient's body is a long object. And, in many instances, only a relatively small sectional region of the long object is of interest. Even if the image of the entire object is needed, it can be obtained by stacking up such sectional regions. It is therefore more practical to employ a spiral scan path just big enough to cover the sectional region rather than to cover the entire object. Under such circumstances, the "short object algorithm" described above may not yield the reconstruction of the sectional region because the cone beam data of the overlaying objects "contaminate" the reconstructed ROI. In particular, contamination results from steps 2 and 3 of the short object algorithm, which spread the cone beam data of the overlaying objects to the reconstructed ROI.

Figure 6:
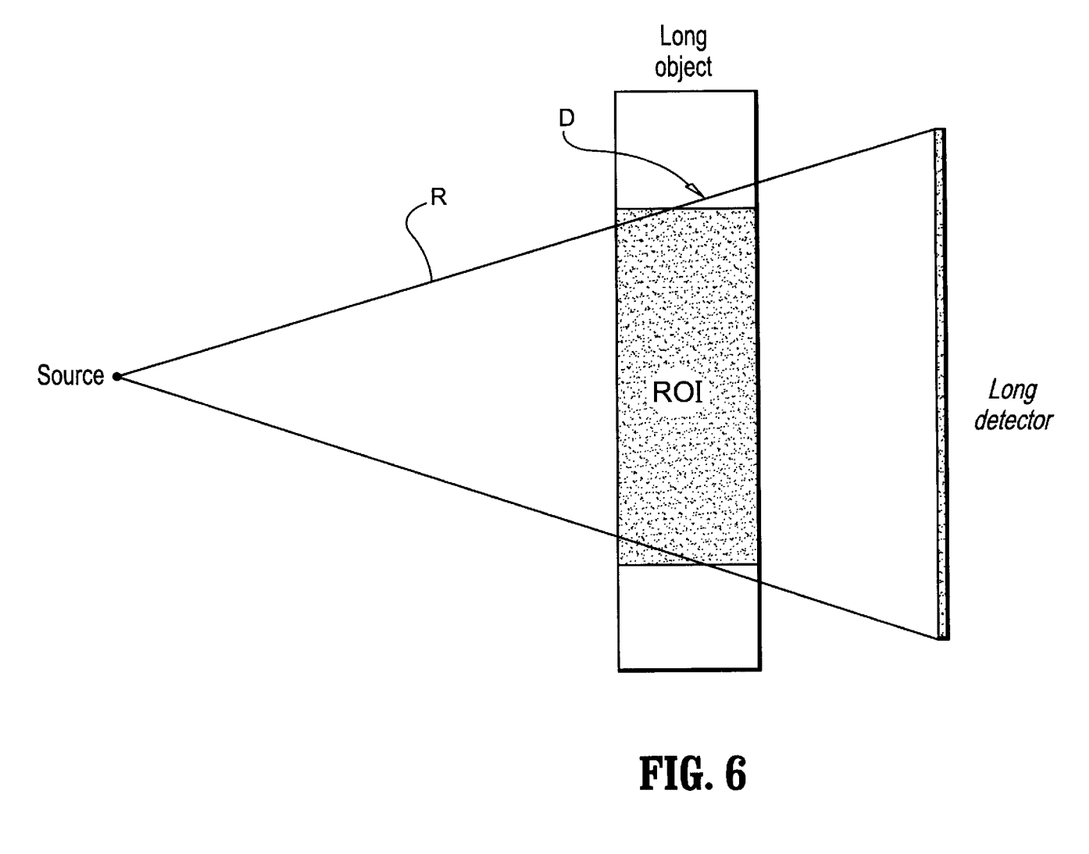
FIG. 6 is a diagram that illustrates a data contamination phenomenon.

FIG. 6 is a schematic diagram that illustrates the principle of data contamination due to overlaying objects. As shown, a ray R, which is emitted from the source to the detector, traverses a portion of the ROI as well as a portion (denoted D) of the long object outside the ROI. To achieve accurate image reconstruction of the ROI, only the data component of ray R data associated with the ROI is desired. Contamination is caused by the data component of ray R associated with the portion D outside the ROI. Therefore, in FIG. 6, the total contamination contained in captured image data of the ROI is due to data that is associated with objects that are located above and below the ROI.

In a spiral scan environment, overlaying objects are "seen" by the source positions in the vicinity of both ends of a spiral scan path. When the short object algorithm is used for image reconstruction of a ROI within a long object, the filtering in step 2 has finite spatial support, and thus the contamination it causes only affects a finite volume near both ends of the ROI. However, the spatial support of the filtering in step 3 of the short object algorithm is infinite, and thus the contamination it causes affects the entire ROI. Thus, in the short object algorithm, it is preferable to modify step 3 in a manner that would achieve more accurate ROI reconstruction in the spiral scan of a long object.

SUMMARY OF THE INVENTION

The present invention is directed to a system and method that accurately reconstructs an image of a ROI (region of interest) within a long object by removing components associated with data contamination.

In one aspect of the present invention, an image reconstruction method comprises the steps of:

collecting a set of image data along a spiral scan path of a ROI (region of interest) portion of an object;

identifying contaminated data within the collected set of image data, the contaminated data corresponding to image data associated with an object outside the ROI;

reconstructing an image of the ROI using the set of image data less the contaminated data.

In another aspect, the step of identifying comprises identifying a source position near a beginning or end portion of the spiral scan path.

In yet another aspect, the step of identifying comprises identifying a first complete sinusoidal stage near a beginning portion of the ROI and a second complete sinusoidal stage near an ending portion of the ROI, wherein a complete sinusoidal stage comprises source positions scanning an angular range of B.

In another aspect of the present invention, the step of identifying the first and second complete sinusoidal stages comprises projecting the spiral path on a plane in Radon space.

In yet another aspect, the step of identifying contaminated data comprises identifying image data associated with a source position that lies on an incomplete sinusoidal stage.

In another aspect of the present invention, a scanning and data acquisition method for three dimensional (3D) computerized tomographic (CT) imaging of a region-of-interest (ROI) in an object, wherein image reconstruction processing is applied to a plurality of sets of 2D cone beam projection data, each set being acquired by irradiation of the object by energy from a cone beam source that is directed to a 2D detector at a corresponding plurality of scan path source positions, comprises the steps of:

applying a mask to each set of the projection data so that data inside the boundaries of each mask form a corresponding plurality of masked 2D data sets;

ramp filtering each masked 2D data set along a plurality of parallel lines formed therein, to generate a corresponding plurality of filtered 2D data, each filtered 2D data set corresponding to a calculation of a first estimate of Radon derivative data determined from a given set of the 2D cone beam projection data;

generating 2D correction data for each of the first estimates of Radon derivative data by processing portions of the given set of cone beam projection data that are adjacent boundaries of the mask, wherein the step of generating 2D correction data is not performed for cone beam projection data that is associated with objects outside a region of interest; and combining each filtered 2D data set and the 2D correction data calculated therefore, in a weighted 3D backprojection manner into a 3D space, thereby reconstructing a 3D image of the ROI in the object.

These and other objects, features and advantages of the present invention will be described or become apparent from the following detailed description of preferred embodiments, which is to be read in connection with the accompanying drawings.

DETAILED DESCRIPTION OF PREFERRED EMBODIMENTS

Figure 4:
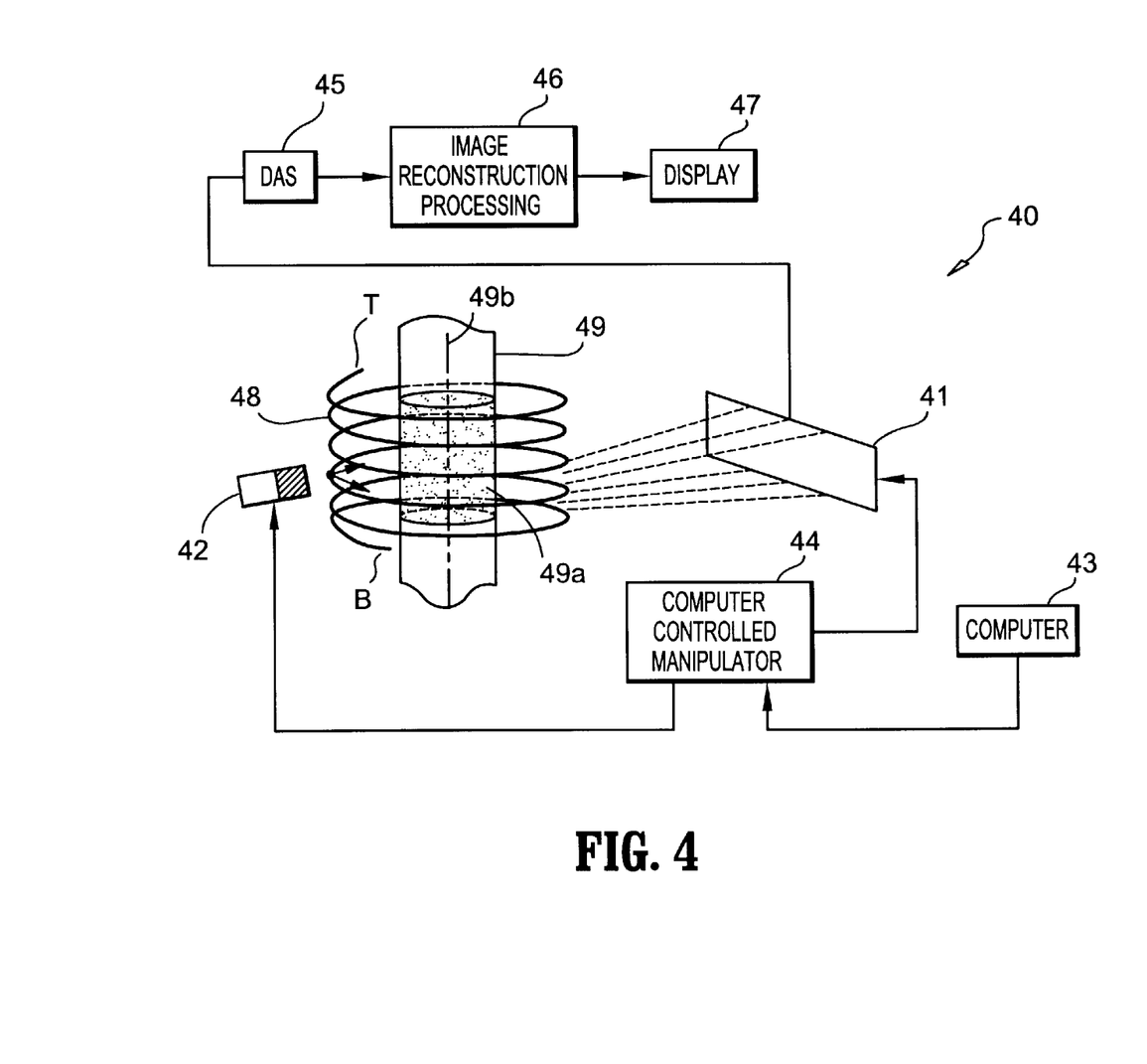
FIG. 4 illustrates a cone beam imaging apparatus that may be employed for performing image reconstruction in accordance with the principles of the invention.

FIG. 4 illustrates a spiral scan cone beam 3D CT imaging system in which an image reconstruction protocol according to the present invention may be implemented for accurately reconstructing a ROI image within a long object. In a preferred embodiment, the imaging system 40 of FIG. 4 is preferably constructed and operates substantially in accordance with the principles described in the above-incorporated U.S. Pat. Nos. 5,257,183 and 6,018,561, except as to be specifically described herein with respect to implementation of an image reconstruction process according to the present invention. In particular, as explained in detail below, a preferred embodiment of the present invention comprises an extension of the image reconstruction protocol described in the above-incorporated U.S. Pat. No. 6,018,561 to enable accurate image reconstruction of an ROI within a long object.

Referring now to FIG. 4, in response to control signals from an appropriately programmed computer 43, a computer controlled manipulator 44 causes a source 42 of a cone or pyramid shaped beam of energy (such as x-rays) and a two-dimensional pixelated detector array 41 to cooperate (scan) at a plurality of discreet, sequentially occurring, adjacent source positions along a pre-defined source scanning path. In the illustrated embodiment the scanning path is shown as a spiral scan path 48 of a ROI 49a, which is centered on a predetermined axis 49b of a long object 49. The figure assumes an upward counterclockwise rotation of the scan path 48 with a beginning portion B near the bottom of the ROI 49a and an ending portion E near the top of the ROI 49a. Further, the spiral scan path 48 is shown as being just big enough to cover the ROI 49a of the long object 49. Other types of scan paths that encircle and traverse object 49 can also be used, however, as will become apparent later, a scan path 48 exhibiting a high degree of symmetry in its parallel projection is preferred.

As a result of the source/detector cooperation under control of computer 43 and manipulator 44, at each of the source positions along path 48, x-ray energy passes through the field of view of the imaging apparatus, is attenuated by object 49a, and a set of projection data corresponding to the sensed x-ray energy falling on the elements (pixels) within detector 212 is developed. Each set of projection data is supplied to a data acquisition system (DAS) 45 which, like the previously described portions of FIG. 4, may operate in a fashion well known to those of ordinary skill in this technology for digitizing and storing of the acquired projection data. An image reconstruction model 46 implements protocols described herein for reconstruction a 3D image from the acquired projection data, which reconstructed 3D image can be displayed on display 47.

As noted above, one embodiment for image reconstruction described in U.S. Pat. No. 6,018,561 comprises the "short object algorithm," wherein image reconstruction processing is applied to a plurality of sets of 2D cone beam projection data, each set being acquired on a 2D detector at a corresponding plurality of scan path source positions. In a preferred embodiment of the present invention, the short object algorithm (which is described in more detail below) is extended for accurately reconstruction an ROI image within a long object.

A first image reconstruction processing step comprises applying a mask to each set of the projection data so that data inside the boundaries of each mask form a corresponding plurality of masked 2D data sets. As described in more detail in the above-incorporated U.S. Pat. No. 6,018,561, the step of applying a mask comprises applying a spiral mask (such as shown in FIG. 5) to each set of the projection data so that data inside the boundaries of each mask form a corresponding plurality of masked 2D data sets. The mask 50 comprises a top curve 51 and a bottom curve 52, each curve being formed by cone beam projections of the spiral scan path turn above and the spiral scanpath turn below the current source position. We shall refer to this mask as a data-combination mask.

More specifically, as noted above, FIG. 4 illustrates a cone beam spiral scan 48 of a region of interest 49a of a long object 49. For a flat detector 41 located at the rotation axis 49b such that the line connecting a source 42 to an origin of the detector 41 is normal to the detector plane, the equation for the top curve for the spiral scan is given by:

$$v = \frac{h}{2\pi} \tan^{-1}\left(\frac{R}{u}\right)\left(1 + \frac{u^2}{R^2}\right) \quad u \geq 0 \quad (1)$$

$$v = \frac{h}{2\pi}\left[\pi + \tan^{-1}\left(\frac{R}{u}\right)\right]\left(1 + \frac{u^2}{R^2}\right) \quad u < 0$$

where u and v are the Cartesian coordinate axes of the detector (as shown in FIG. 5) with the v axis coinciding with the rotation axis, R is the radius of the spiral, and h is the distance between adjacent spiral turns (the pitch). The bottom curve is the reflection of the top curve about the origin, i.e. (u,v)->(-u,-v). The shape of the spiral mask is shown in FIG. 5.

In accordance with the general principles of masking, data in the set that is outside the mask is changed to a zero value, while data that is inside the mask is left unchanged. After a set of projection data is appropriately masked, it is referred to as a masked set of projection data, or more simply as a masked data set. Since the masks are formed by cone beam projection of the spiral turn above and the turn below the current source position, the masked data set corresponds exactly to the angular range bound by the prior and the subsequent source positions, as required by the data combination principles.

A second step comprises 1D ramp filtering of each masked 2D data set along a plurality of parallel lines formed therein, to generate a corresponding plurality of filtered 2D data sets. Each filtered 2D data set is a calculation of a first estimate of Radon derivative data determined from a given set of the 2D cone beam projection data. More specifically, a Feldkamp ramp filtering technique is applied to the masked sets of projection data, wherein each set of masked data is ramp filtered along a plurality of parallel lines (t) formed therein, which lines are parallel with and in the direction of a parallel projection into the data set of a line that is tangent to the scan path at the source position that acquired that data set and in the direction of the next source position. Ramp filtering of each masked data set along lines (t) generates a corresponding plurality of filtered data sets, where the data at each point along each line represents a summation of the Radon data at that point.

A third step comprises developing 2D correction data for each of the first estimates of Radon derivative data by processing portions of the given set of cone beam projection data that are adjacent boundaries of the mask. A fourth step comprises combining each filtered 2D data set and the 2D correction data calculated therefore, in a weighted 3D back-projection manner into a 3D space, thereby reconstructing a 3D image of the ROI in the object.

In accordance with the principles of the present invention, an extension to the "short object algorithm" described above is implemented to eliminate/mitigate data contamination. In a preferred embodiment, step 3 of the above process is modified to achieve ROI reconstruction in the spiral scan of a long object, wherein those source positions near both ends of the spiral scan path (e.g., portions B and T of the spiral scan path 48 shown in FIG. 4) which see the overlaying objects are first identified, and step 3 is skipped in processing the associated cone beam data. A process for identifying contamination data will now be described in detail, with references to FIGS. 7–12.

Figure 7:
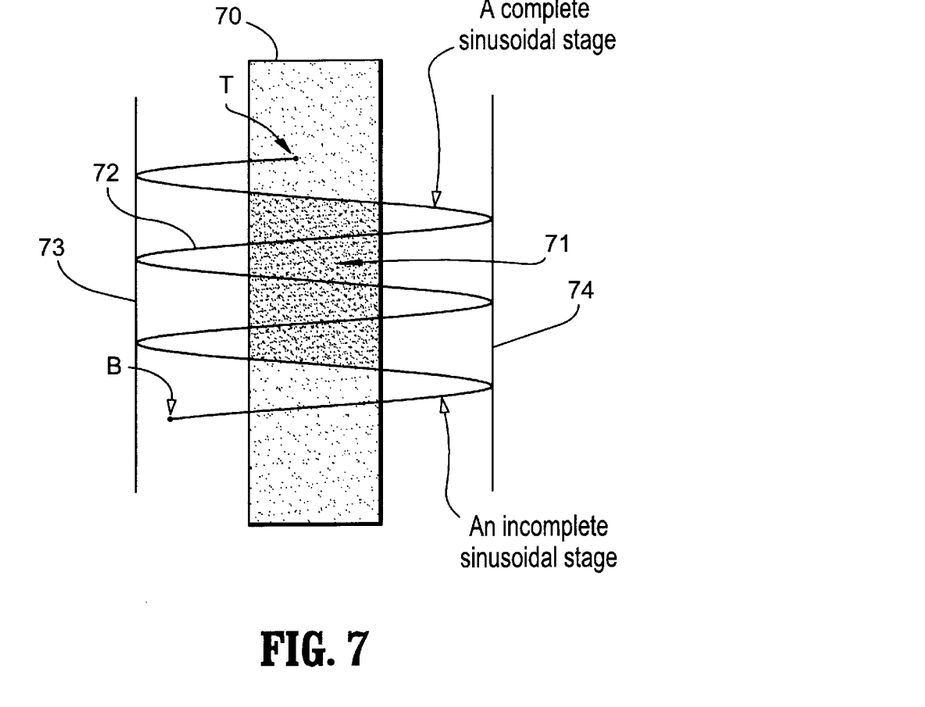
FIG. 7 is a diagram of an exemplary region of interest defined by a spiral path projection to illustrate principles of the present invention.
Figures 8A, 8B:
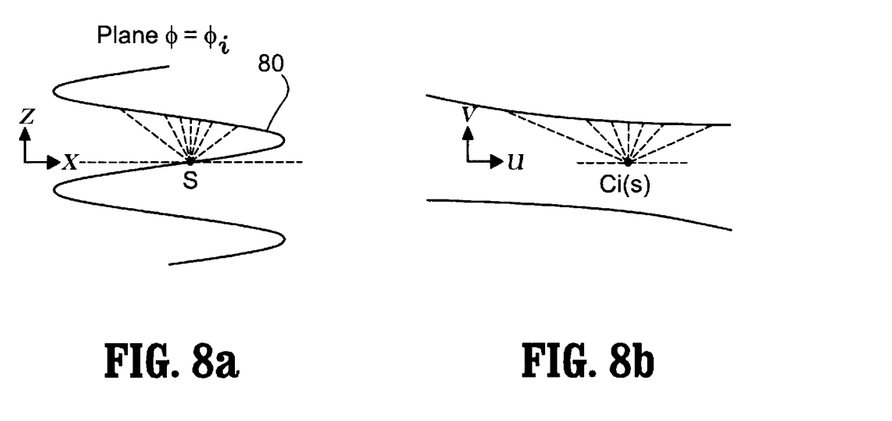
FIGS. 8a and 8b are exemplary diagrams that illustrate a correspondence between integration line segments on a detector and line integral intervals on a plane.

FIG. 7 is an exemplary diagram that illustrates a local region of interest (ROI) 71 (of long object 70) defined by a spiral path projection 72. FIGS. 8a and 8b illustrate a correspondence between an integration line segment on a detector and line integral interval on a N plane. A "N plane" as defined herein is a plane in Radon space that contains the z axis oriented at an azimuthal angle N.

FIG. 8a specifically illustrates a N plane=$N_i$, wherein the illustrated sine curve 80 comprises a projection of the spiral path 72 on the N plane from a source position S. In particular, the parallel projection of the spiral path 72 on a N plane is in the form of a sinusoidal curve 80 bound between the projection of the two side edges (73 and 74) of a spiral cylinder effectively defined by the spiral scan path 72. The phase of the sinusoidal 80 is dependant on the orientation of the N plane. The dotted lines in FIG. 8a from S (source position) represent all line integral intervals on the $N_i$ plane that intersect S on the spiral scan path (the line integral intervals represent the data generated on the $N_i$ plane the source position S.

FIG. 8b illustrates a detector plane, representing an image generated at source position S. The term $C_i(s)$ corresponds to plane N=$N_i$ at source position S. The dotted lines on the detector in FIG. 8b are integration line segments that correspond to the line integral intervals in FIG. 8a.

In FIG. 7, various portions of the sinusoidal partitioned by the side edges 73, 74 are referred to herein as "sinusoidal stages". As shown in FIG. 7, a sinusoidal stage is deemed "complete" if both ends of the sinusoidal state are in touch with the side edges 73, 74, otherwise the sinusoidal stage is deemed "incomplete". A "complete" sinusoidal stage contains source positions covering an angular range of B.

In accordance with the present invention, on each N plane, the top and the bottom edges of a local ROI are defined by the uppermost and the lowermost "complete" sinusoidal stages of the spiral path projection, as illustrated in FIG. 7. A reconstructed (global) ROI is formed by the intersection of all local ROI's.

From a theoretical point of view, the filtering steps (step 2 and step 3) of the above-described "short object" algorithm are essentially equivalent to a filtering process involving all integration line segments on the detector (FIG. 8b). As noted above, FIGS. 8a and 8b show the correspondence between line integral intervals on a N plane an integration line segment on the detector. Accordingly, the filtering processes applied to the set of line segments that intersect at a common point on the u axis (of the detector) (FIG. 8b) generates a corresponding set of line integral intervals on a N plane (FIG. 8a). This correlation between a N plane and a location on the u axis is described in detail, for example, in the above incorporated U.S. Pat. No. 5,257,183. Since the set of line segments on the detector (FIG. 8b) are limited at the mask boundary, the set of line integral intervals on the N plane (FIG. 8a) are limited at the next sinusoidal stage above and below the current source position. Furthermore, a line segment on the detector bounded between the u axis and the upper/lower the mask boundary corresponds to a line integral interval on the N plane bounded between the current source position and the upper/lower sinusoidal stage.

Consider a source position S in the views [0, B] (i.e., a first half of a spiral circle) measured from the end T of the spiral path, as shown in FIG. 7. The source position S projects onto some N planes onto the uppermost complete stage of the spiral path projection. The line integral intervals on the N planes below S illuminate the local ROI 71, whereas the line integral intervals on the N plane above S illuminate the objects outside the local ROI 71. Due to the correspondence between integration line segment on the detector and line integral interval on a N plane (as illustrated in FIG. 8) to reconstruct the local ROI on these N planes, only the portion of cone beam data below the u axis on the detector are utilized because the portion of cone beam data above the u axis illuminate the objects outside the local ROI and, thus, contribute to the contamination of the ROI. Thus, for these N planes, step 3 of the short object algorithm is applied to only the lower mask boundary in filtering the cone beam data at S.

On the other N planes, S1 projects outside the uppermost complete stage of the spiral path projection. For these N planes, all the cone beam data of S illuminate the objects outside the local ROI and therefore contribute to the contamination of the ROI. Thus for these N planes, step 3 of the short object algorithm is skipped entirely in filtering the cone beam data at 51.

Consider a source position S in the views [B, 2B] measured from the end of the spiral path. S projects onto some N planes onto the uppermost complete stage of the spiral path projection. The line integral intervals on the N planes below S illuminate the local ROI, and the line integral intervals on the N plane above S illuminate the objects outside the local ROI. Due to the correspondence between integration line segment on the detector and line integral interval on a N plane as illustrated in FIG. 8, for the reconstruction of the local ROI on these N planes, only the portion of cone beam data below the u axis on the detector are needed; the portion of cone beam data above the u axis illuminate the objects outside the local ROI and therefore contribute to the contamination of the ROI. Thus, for these N planes, step 3 is applied to only the lower mask boundary in filtering the cone beam data at S.

On the other N planes, S projects inside the uppermost complete stage of the spiral path projection. For these N planes, all the cone beam data of S illuminate the local ROI and therefore do not contribute to the contamination of the ROI. Thus, for these N planes, no modification of step 3 is needed in filtering the cone beam data at S.

In the following description of preferred embodiments, a detailed discussion will be provided regarding the grouping processes for the source positions in the view angular range [0, B] and those in the view angular range [B, 2B], both measured from the end of the spiral path (e.g., T in FIG. 7). The grouping processes for the source positions near the start of the spiral path (e.g., B in FIG. 7) is similar except for obvious modifications. In the following analysis, it is assumed that the sense of the rotation of the source along the spiral is anticlockwise up. The analysis can be readily modified for the opposite sense of source rotation.

Figure 9:
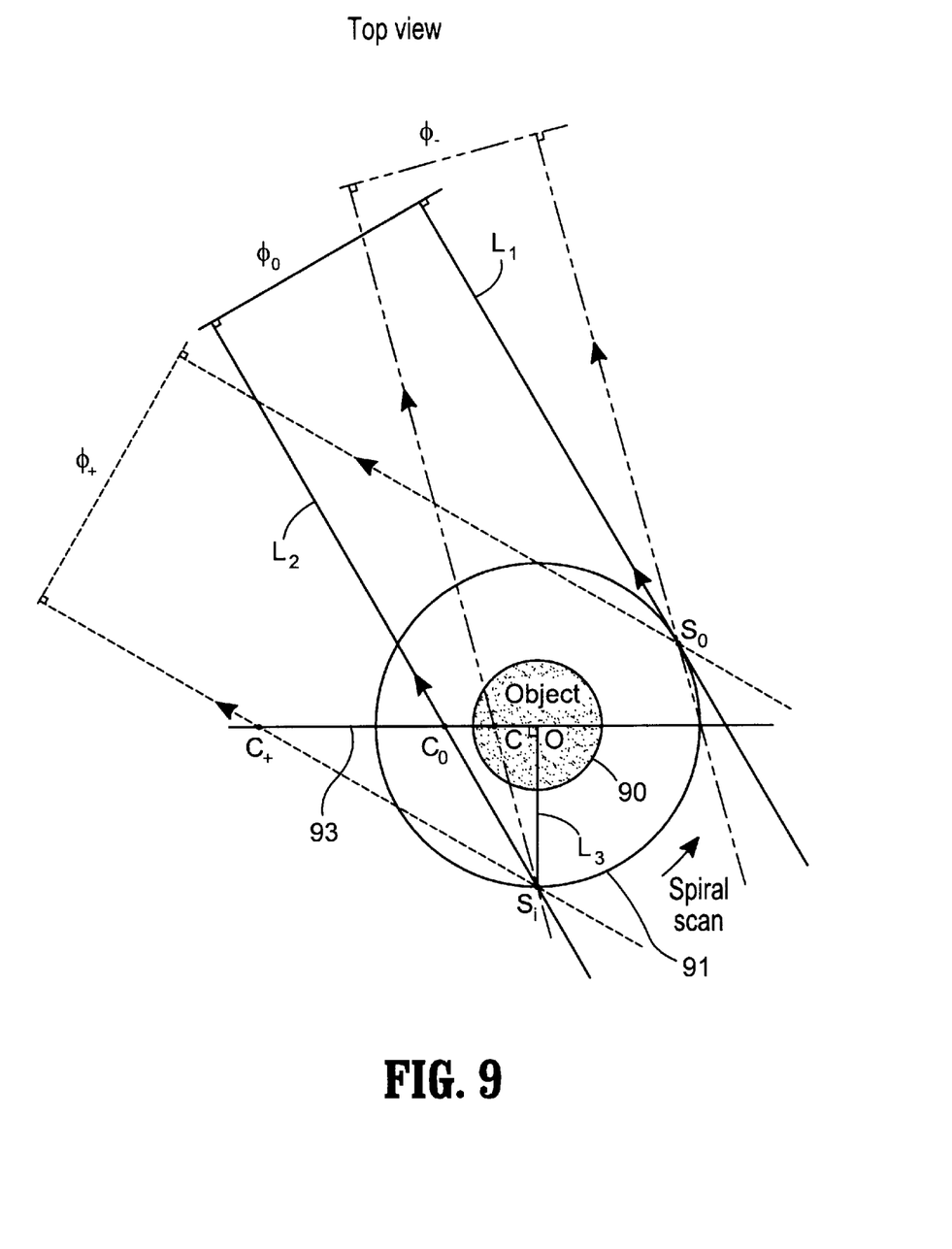
FIG. 9 is an exemplary diagram showing various source positions in an angular range [0, B] from the end of a spiral scan path, illustrating principles of the present invention.

1. View angular range [0, B] from spiral end Referring now to FIG. 9, a diagram illustrates various source positions in the angular range [0, B]. More specifically, FIG. 9 illustrates a top view wherein circle 90 represents of an object 90 being imaged from a source position $S_i$ in the view angular range [0, B] measured from a spiral end source position $S_0$. The circle 91 represents the spiral path traversed by the x ray source S. In FIG. 9, a line L1 starting from ending source position $S_o$ is tangential to spiral scan circle 91. The Radon space N plane that forms an orthogonal intersection with line L1 defines the Radon space $N_o$ plane. Assuming anti-clockwise rotation of the source, source position $S_i$ is marked on circle 91. A line L2 that passes through $S_i$ is parallel with L1 and, therefore, bears an orthogonal relationship with the Radon space $N_o$ plane. The point $C_o$ is defined as the point at which the line L2 intersects the u-axis of the detector that acquires the cone beam data at source position $S_i$. The detector plane 93 that acquires the cone beam data at $S_i$ is determined by its orthogonal relationship to line L3 that extends from source position $S_i$ to the center of the object 90.

Figure 10A:
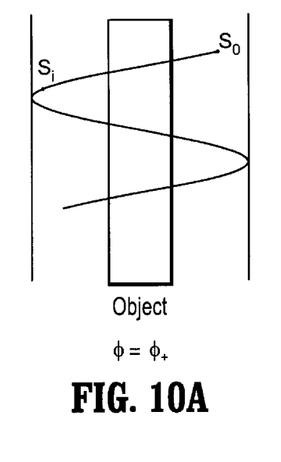
FIGS. 10a, 10b and 10c are exemplary diagrams illustrating projections of the spiral path on the various planes shown in FIG. 9, illustrating principles of the present invention.
Figure 10B:
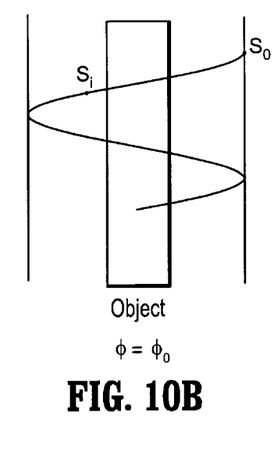
Figure 10C:
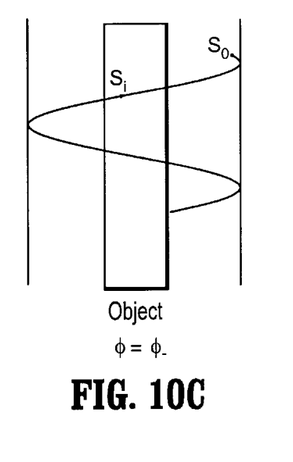

FIGS. 10a, 10b and 10c respectively illustrate projections of the spiral path on $N_+$, $N_o$ and $N_-$ planes shown in FIG. 9 (viewing the spiral path in FIG. 9 from three different angles). As shown in FIG. 10b, in the direction $N_o$, the end source position $S_o$ projects onto the edge of the spiral cylinder. Also shown in FIG. 9 and 10 are two directions $N_+$ and $N_{31}$ incrementally rotated from $N_o$ in the opposite directions. As shown in FIG. 10a, in the direction $N_+$, the spiral path portion containing $S_i$ and ending at $S_o$ does not touch the tangent to the spiral cylinder on the right hand side. Therefore on the $N=N_+$ plane, the sinusoidal stage on which the current source position $S_i$ projects does not reach both edges of the spiral cylinder projection, as illustrated in FIG. 10A, and thus this sinusoidal stage is incomplete. In other words, since $S_o$ does not touch the edge of the spiral cylinder on the right side, the top segment of the spiral turn is incomplete (i.e., less than B) Consequently, on this plane, the uppermost complete sinusoidal stage which defines the top edge of the local ROI is the stage beneath, as shown in FIG. 10a. Since the projection of $S_i$ lies outside the local ROI, $S_i$ contributes to the contamination of the local ROI on the $N=N_+$ plane. In other words, because $S_i$ is located on an incomplete segment, the data from $S_i$ is not considered.

On the other hand, in the direction $N_-$, the spiral path portion containing $S_i$ and ending at $S_0$ touches the tangent to the spiral cylinder on the right hand side. Therefore, on the $N=N_-$ plane, the sinusoidal stage on which the current source position $S_i$ projects reaches both edges of the spiral cylinder projection, as illustrated in FIG. 10C, and thus this sinusoidal stage is complete. Consequently, on this plane, the projection of $S_i$ lies on the uppermost complete sinusoidal stage which defines the top edge of the local ROI on the $N=N_-$ plane, as shown in FIG. 10c.

Referring again to FIG. 9, let the points $C_0$, $C_+$, and $C_-$ on the u axis respectively denote the projection on the detector of the current source position in the direction $N_0$, $N_+$, and $N_-$. The points $C_+$ and $C_-$ are respectively to the left and to the right of $C_0$. All the Radon derivative data generated on the $N=N_+$ plane using the cone beam data detected at $S_i$ come from integration line segments that intersect $C_+$. As discussed above for FIG. 10a, since $S_i$ contributes to the contamination of the local ROI on the $N=N_+$ plane, to avoid contamination, the boundary/correction term at both the upper and lower mask boundary is preferably skipped for integration line segments intersecting $C_+$. And by extension of step 3 of the short object algorithm, the boundary/correction term at both the upper and lower mask boundary is preferably skipped for integration line segments intersecting to the left of $C_0$ on the u axis.

On the other hand, all the Radon derivative data generated on the $N=N_-$ plane using the cone beam data detected at $S_i$ come from integration line segments that intersect $C_-$. As discussed above for FIG. 10c, since the projection of $S_i$ lies on the uppermost complete sinusoidal stage which defines the top edge of the local ROI on the $N=N_-$ plane, the portion of the cone beam data above the u axis contributes to the contamination of the local ROI. Consequently to avoid contamination, the boundary/correction term at the upper mask boundary is preferably skipped for integration line segments that intersect $C_-$, and by extension, the boundary/correction term at the upper mask boundary is preferably skipped for integration line segments that intersect to the right of $C_0$ on the u axis.

Figure 11:
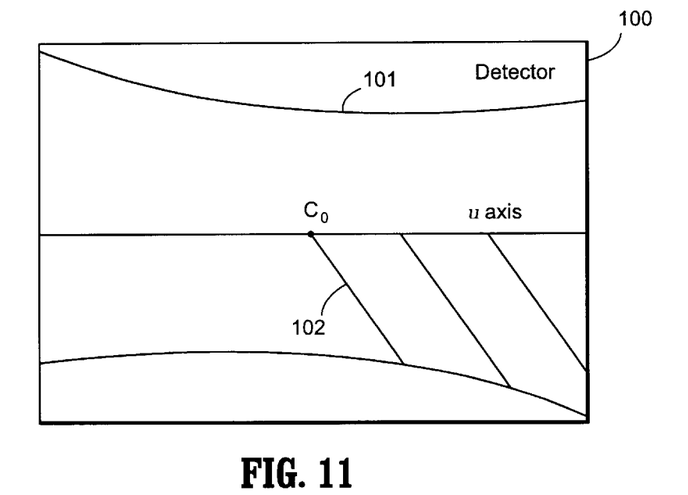
FIG. 11 is a diagram of a mask region illustrating the portion of the mask boundary that is filtered for source positions in an angular range of [0, B] from the end of a spiral scan path.

FIG. 11 is a diagram that illustrates a portion of a mask boundary to which a filtering step (step 3) is applied for source positions in the angular range [0, B] from the spiral end. In other words, the diagram of FIG. 11 summarizes how the boundary/correction term is skipped for the cone beam images in the view angular range [0, B] measured from the spiral end. Integration line segments are shown for an arbitrary projection angle 2.

More specifically, in FIG. 11, a set of cone bean data 100 acquired at a given source position $S_i$, the point Co is marked on the u axis of detector. The data combination mask 101 is applied to the cone beam data 100, and a plurality of lines 102 are formed in the set of cone beam data 100 (as discussed above). Generally, the endpoints (and thus length) of the lines 102 are determined by the outer boundaries of the data combination mask 101 for all source positions that are internal of the top and bottom 2B angular range in the scan path that are near the top and bottom edges, respectively, of the ROI. However, as shown in FIG. 11, the line segments that which cross the u axis to the right of point Co (corresponding to FIG. 10c) have their endpoints determined by one of lower boundary of the mask and the u axis, and all of the line segments crossing the u axis to the left of Co (corresponding to FIG. 10a) are not used. In other words, the boundary/correction term at the upper mask boundary is skipped for line segments which intersect the u axis to the right of $C_0$, and the boundary/correction term at both the upper and lower mask boundary is skipped for line segments which cross the u axis to the left of $C_0$. The process is repeated for all 2.

2. View angular range [B, 2B] from spiral end

Figure 12:
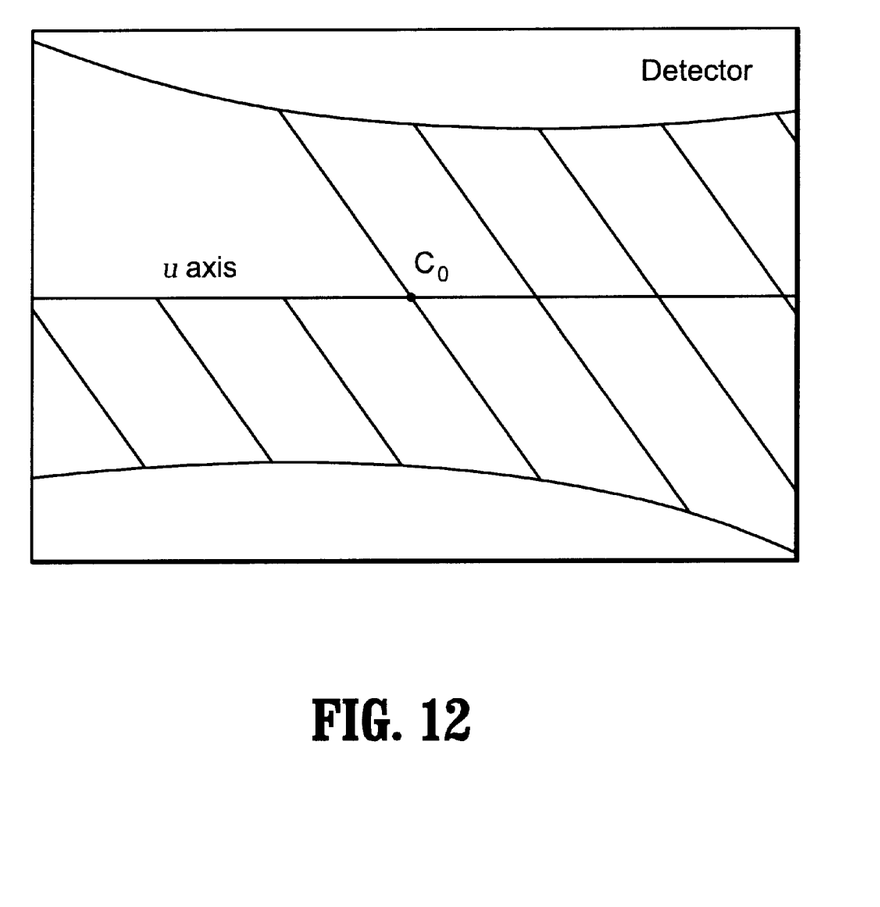
FIG. 12 is a diagram of a mask region illustrating the portion of the mask boundary that is filtered for source positions in an angular range of [B, 2B] from the end of a spiral scan path.

The above analysis can be made in a similar manner as in the case of view angular range [B, 2B], and a detailed analysis is not necessary to understanding the invention. FIG. 12 summarizes how the boundary/correction term is skipped for the cone beam images in the view angular range [B, 2B] measured from the spiral end. The point $C_0$ is constructed as illustrated in FIG. 9. Integration line segments are shown for an arbitrary projection angle 2. The boundary/correction term at the upper mask boundary is skipped for line segments that intersect the u axis to the left of $C_0$. The process is repeated for all 2.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. An image reconstruction method comprising the steps of:
    collecting a set of image data along a spiral scan path of a ROI (region of interest) portion of an object;
    identifying contaminated data within the collected set of image data, the contaminated data corresponding to image data associated with an object outside the ROI; and
    reconstructing an image of the ROI using the set of image data less the contaminated data.

2. The method of claim 1, wherein the step of identifying comprises identifying a source position near a beginning or end portion of the spiral scan path.

3. The method of claim 1, wherein the step of identifying comprises identifying a first complete sinusoidal stage near a beginning portion of the ROI and a second complete sinusoidal stage near an ending portion of the ROI, wherein a complete sinusoidal stage comprises source positions scanning an angular range of B.

4. The method of claim 3, wherein the step of identifying the first and second complete sinusoidal stages comprises projecting the spiral path on a plane in Radon space.

5. The method of claim 3, wherein the step of identifying contaminated data comprises identifying image data associated with a source position that lies on an incomplete sinusoidal stage.

6. A scanning and data acquisition method for three dimensional (3D) computerized tomographic (CT) imaging of a region-of-interest (ROI) in an object, wherein image reconstruction processing is applied to a plurality of sets of 2D cone beam projection data, each set being acquired by irradiation of the object by energy from a cone beam source that is directed to a 2D detector at a corresponding plurality of scan path source positions, comprising the steps of:
    applying a mask to each set of the projection data so that data inside the boundaries of each mask form a corresponding plurality of masked 2D data sets;
    ramp filtering each masked 2D data set along a plurality of parallel lines formed therein, to generate a corresponding plurality of filtered 2D data, each filtered 2D data set corresponding to a calculation of a first estimate of Radon derivative data determined from a given set of the 2D cone beam projection data;
    generating 2D correction data for each of the first estimates of Radon derivative data by processing portions of the given set of cone beam projection data that are adjacent boundaries of the mask, wherein the step of generating 2D correction data is not performed for cone beam projection data that is associated with objects outside a region of interest; and
    combining each filtered 2D data set and the 2D correction data calculated therefore, in a weighted 3D backprojection manner into a 3D space, thereby reconstructing a 3D image of the ROI in the object.

7. The method of claim 6, comprising the step of identifying contaminated data within the set of cone beam projection data, the contaminated data corresponding to cone beam projection data associated with an object outside the ROI.

8. The method of claim 7, wherein the step of identifying comprises identifying a source position near a beginning or end portion of the spiral scan path.

9. The method of claim 7, wherein the step of identifying comprises identifying a first complete sinusoidal stage near a beginning portion of the ROI and a second complete sinusoidal stage near an ending portion of the ROI, wherein a complete sinusoidal stage comprises source positions scanning an angular range of B.

10. The method of claim 9, wherein the step of identifying the first and second complete sinusoidal stages comprises projecting the spiral path on a plane in Radon space.

11. The method of claim 9, wherein the step of identifying contaminated data comprises identifying image data associated with a source position that lies on an incomplete sinusoidal stage.

12. A program storage device readable by a machine, tangibly embodying a program of instructions executable by the machine to perform method steps for performing three dimensional (3D) computerized tomographic (CT) image reconstruction of a region-of-interest (ROI) in an object, wherein image reconstruction processing is applied to a plurality of sets of 2D cone beam projection data, each set being acquired by irradiation of the object by energy from a cone beam source that is directed to a 2D detector at a corresponding plurality of scan path source positions, the method steps comprising:

applying a mask to each set of the projection data so that data inside the boundaries of each mask form a corresponding plurality of masked 2D data sets;

ramp filtering each masked 2D data set along a plurality of parallel lines formed therein, to generate a corresponding plurality of filtered 2D data, each filtered 2D data set corresponding to a calculation of a first estimate of Radon derivative data determined from a given set of the 2D cone beam projection data;

generating 2D correction data for each of the first estimates of Radon derivative data by processing portions of the given set of cone beam projection data that are adjacent boundaries of the mask, wherein the step of generating 2D correction data is not performed for cone beam projection data that is associated with objects outside a region of interest; and combining each filtered 2D data set and the 2D correction data calculated therefore, in a weighted 3D backprojection manner into a 3D space, thereby reconstructing a 3D image of the ROI in the object.

13. The program storage device of claim 12, comprising instructions for performing the step of identifying contaminated data within the set of cone beam projection data, the contaminated data corresponding to cone beam projection data associated with an object outside the ROI.

14. The program storage device of claim 13, wherein the instructions for performing the step of identifying comprise instructions for identifying a source position near a beginning or end portion of the spiral scan path.

15. The program storage device of claim 13, wherein the instructions for performing the step of identifying comprise instructions for identifying a first complete sinusoidal stage near a beginning portion of the ROI and a second complete sinusoidal stage near an ending portion of the ROI, wherein a complete sinusoidal stage comprises source positions scanning an angular range of B.

16. The program storage device of claim 15, wherein the instructions for performing the step of identifying the first and second complete sinusoidal stages comprise instructions for projecting the spiral path on a plane in Radon space.

17. The program storage device of claim 15, wherein the instructions for performing the step of identifying contaminated data comprise instructions for identifying image data associated with a source position that lies on an incomplete sinusoidal stage.

18. An apparatus for three dimensional (3D) computerized tomographic (CT) imaging of a region-of-interest (ROI) in an object, comprising:

a cone beam source for applying radiation energy to at least the ROI of the object;

a 2D area detector for detecting radiation energy;

means for defining a source scanning trajectory as a scan path traversed by the source;

a manipulator for causing the cone beam source, fixed relative to an area detector with both source and detector movably positioned relative to the object, to scan about the ROI in the object at a plurality of source positions in a direction along the scan path to cause said area detector to acquire a set of 2D cone beam projection data at each of said source positions;

a masking means for applying a mask to each set of the 2D cone beam projection data to generate masked data sets;

a ramp filtering means for ramp filtering each masked 2D data set along a plurality of parallel lines formed therein, to generate a corresponding plurality of filtered 2D data, each filtered 2D data set corresponding to a calculation of a first estimate of Radon derivative data determined from a given set of the 2D cone beam projection data;

processing means for developing 2D correction data for each of the first estimates of Radon derivative data by processing portions of the given set of 2D cone beam projection data that are adjacent boundaries of the mask, wherein 2D correction data is not generated for cone beam projection data that is associated with objects outside a region of interest; and 3D backprojection means for combining each filtered 2D data set and the 2D correction data calculated therefore, in a weighted 3D backprojection manner into a 3D space, thereby reconstructing a 3D image of the ROI in the object.

* * * * *